United States Patent [19]
Lustig et al.

[11] Patent Number: 5,208,933
[45] Date of Patent: May 11, 1993

[54] DENTAL TOOL WITH LIQUID DISPENSING, AND CARTRIDGE

[75] Inventors: L. Paul Lustig, 304 Greenwood St., Newton, Mass. 02159; Andrew Tybinkowski, Boxford, Mass.

[73] Assignee: L. Paul Lustig, Newton Centre, Mass.

[21] Appl. No.: 686,793

[22] Filed: Apr. 17, 1991

Related U.S. Application Data

[63] Continuation-in-part of Ser. No. 611,898, Nov. 9, 1990, Pat. No. 5,142,723.

[51] Int. Cl.⁵ .................... A61C 17/28; A61C 17/36; A46B 13/04
[52] U.S. Cl. .......................... 15/22.1; 15/24; 15/29; 401/163; 401/169
[58] Field of Search .............. 15/24, 29, 22.1, 22.2; 433/125; 401/134, 152, 153, 158, 161, 163, 168, 169; 222/95, 106, 192

[56] References Cited

U.S. PATENT DOCUMENTS

| | | |
|---|---|---|
| 1,476,433 | 12/1923 | Vandervoort . |
| 2,162,447 | 6/1939 | Seibel ............................ 221/60 |
| 2,820,979 | 1/1958 | Herter ............................ 15/135 |
| 3,056,151 | 10/1962 | Vlacancich ...................... 15/29 |
| 3,137,305 | 6/1964 | Jones ............................ 401/153 |
| 3,148,684 | 9/1964 | Keeler . |
| 3,178,754 | 4/1965 | Cleverdon . |
| 3,261,367 | 9/1963 | Pickering ...................... 132/84 |
| 3,903,888 | 9/1975 | Buelow et al. ................ 128/222 |
| 3,910,265 | 10/1975 | Coleman ...................... 128/66 |
| 4,013,370 | 3/1977 | Gingras ........................ 401/175 |
| 4,049,354 | 9/1977 | O'Rourke ..................... 401/134 |
| 4,060,870 | 12/1977 | Cannarella .................... 15/24 |
| 4,155,663 | 5/1979 | Cerquozzi ..................... 401/135 |
| 4,173,828 | 11/1979 | Lustig et al. .................. 433/87 |
| 4,221,492 | 9/1980 | Boscardin et al. ............. 401/184 |
| 4,236,651 | 12/1980 | Meyer et al. .................. 222/82 |
| 4,315,741 | 2/1982 | Reichl ........................... 433/125 |
| 4,375,924 | 3/1983 | Lemire ......................... 401/173 |
| 4,384,645 | 5/1983 | Manfredi ...................... 206/229 |
| 4,484,893 | 11/1984 | Finn ............................. 433/118 |
| 4,527,574 | 7/1985 | Manfredi ...................... 132/84 B |
| 4,583,563 | 4/1986 | Turner .......................... 132/84 R |
| 4,695,177 | 9/1987 | Kuo ............................. 401/150 |
| 4,717,278 | 1/1988 | Kemeny ....................... 401/286 |
| 4,759,381 | 7/1988 | Cesari .......................... 132/84 B |
| 4,845,795 | 7/1989 | Crawford et al. ............. 15/22.1 |
| 4,880,382 | 11/1914 | Moret et al. .................. 433/118 |

*Primary Examiner*—Edward L. Roberts
*Attorney, Agent, or Firm*—Lahive & Cockfield

[57] ABSTRACT

A powered dental tool dispenses a liquid dentifrice from a removable and replaceable cartridge to a dental site being cleaned or otherwise treated. The tool mounts the cartridge to receive a supply of the dispensable liquid, and accommodates the removal and replacement of a spent cartridge. A removable and replaceable cartridge for supplying dispensable liquid to a dental tool is initially sealed, is readily installed in the tool with a connection to a dispensing tube, and is collapsible for emptying it. A multiple-treatment dental care system has a single power handle that operates interchangeable with a fluid dispensing spray implement, with a rotary treatment implement, and with a revolving-bristle brush implement. In addition to dispensing fluid with the spray implement, the system can dispense liquid material to the dental site being treated by way of the rotary implement and by way of the revolving brush implement.

17 Claims, 6 Drawing Sheets

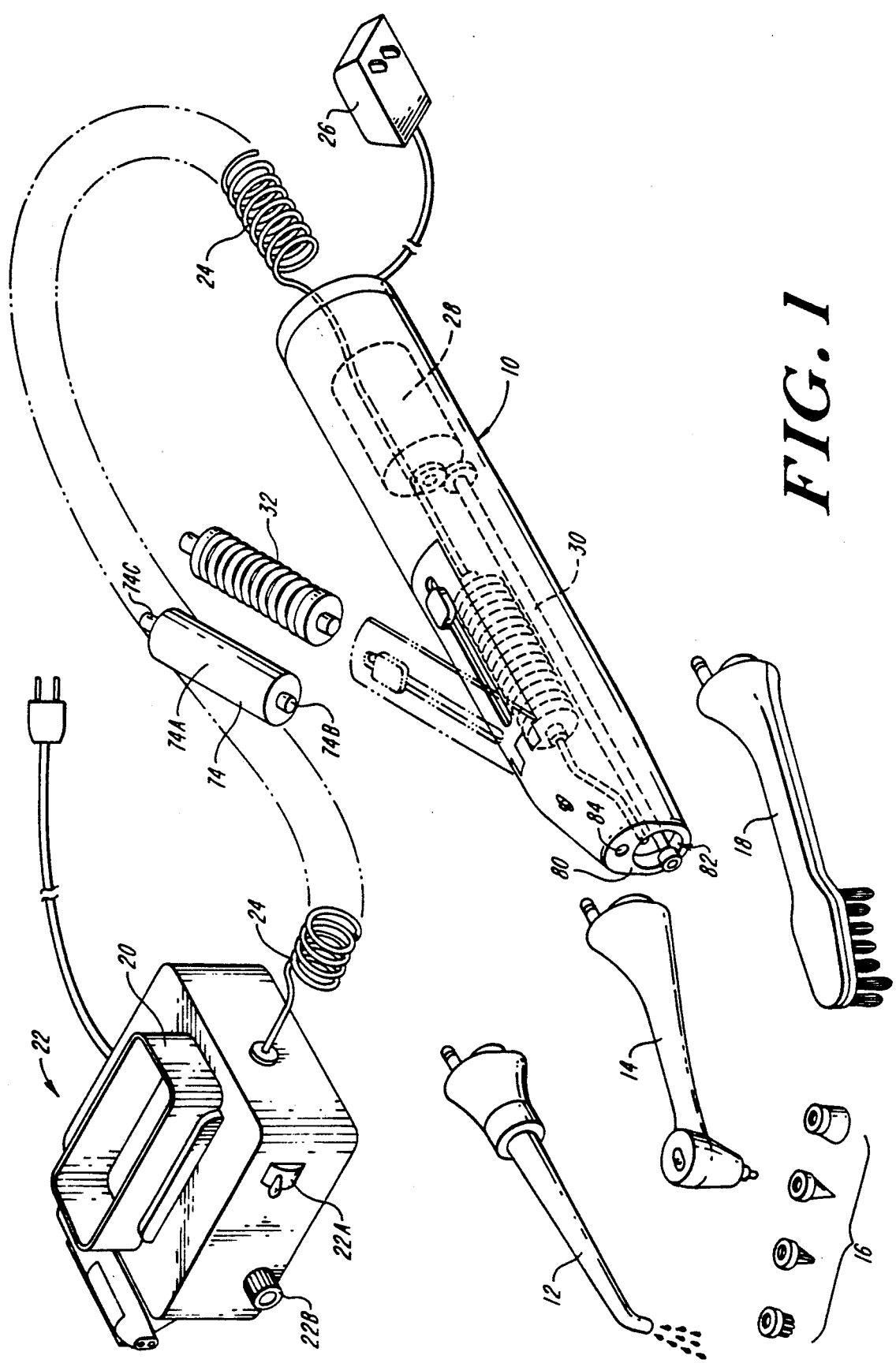

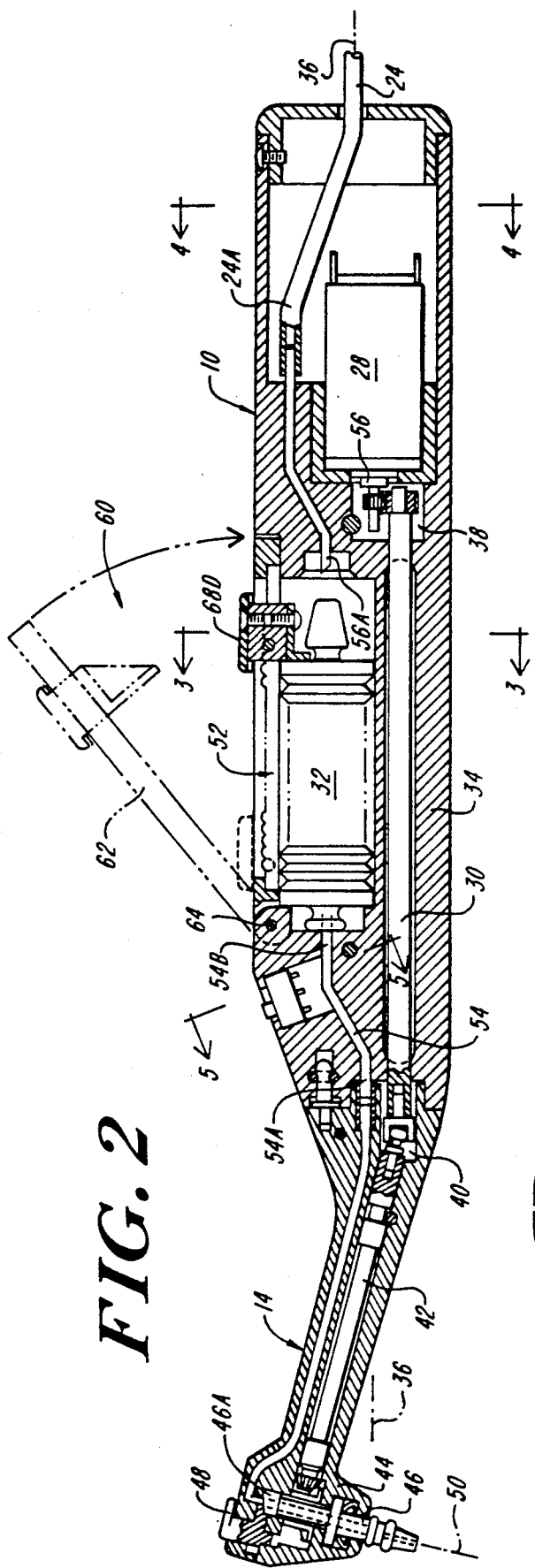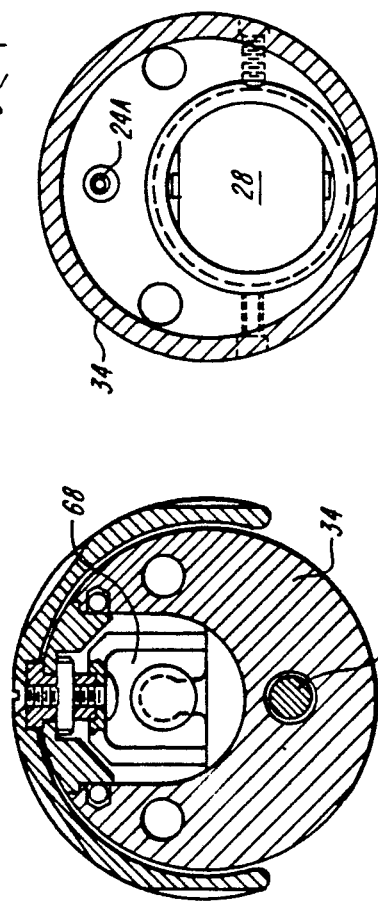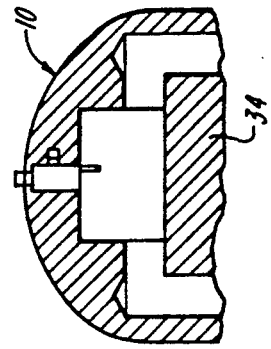

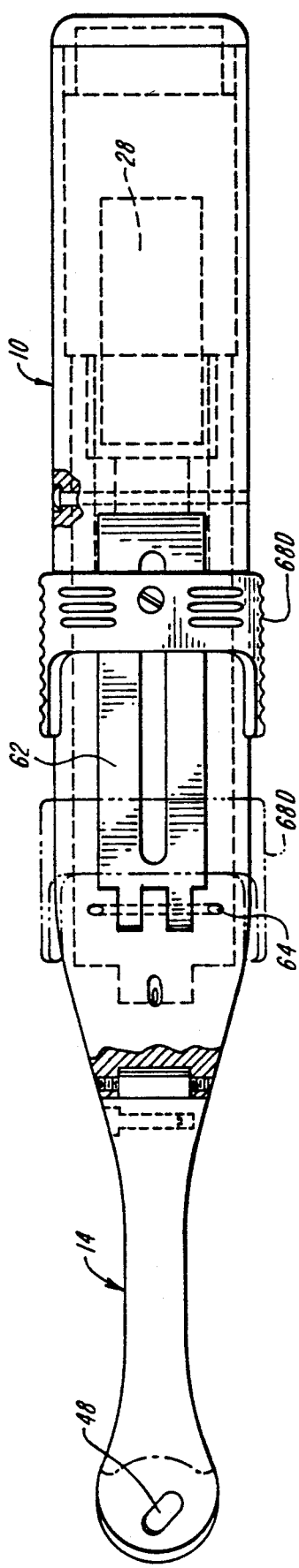
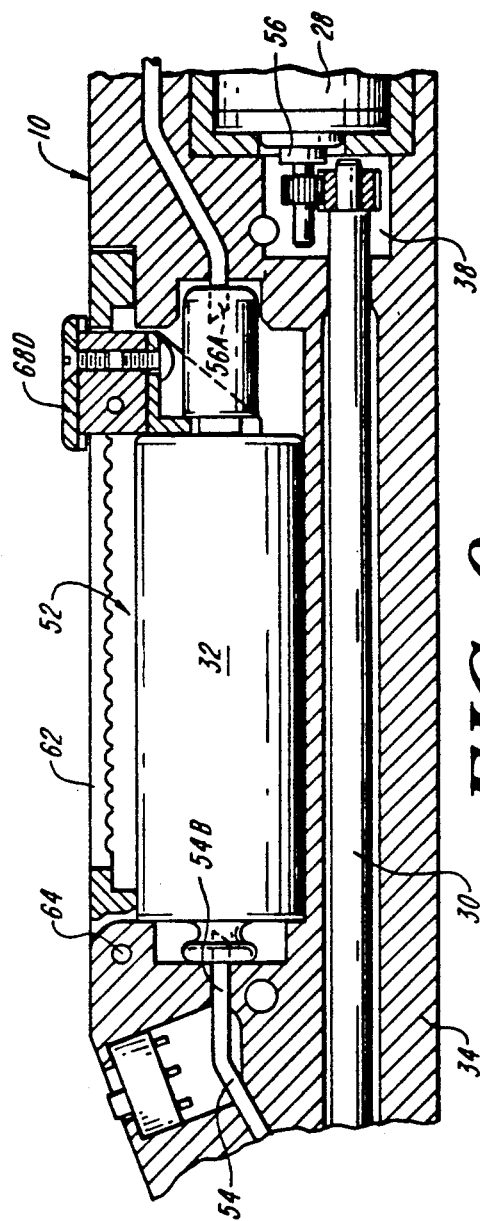
FIG. 6
FIG. 9

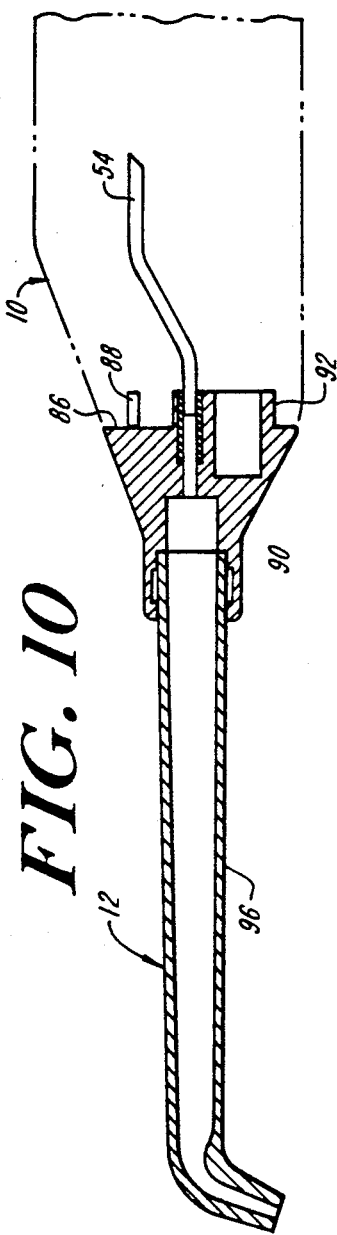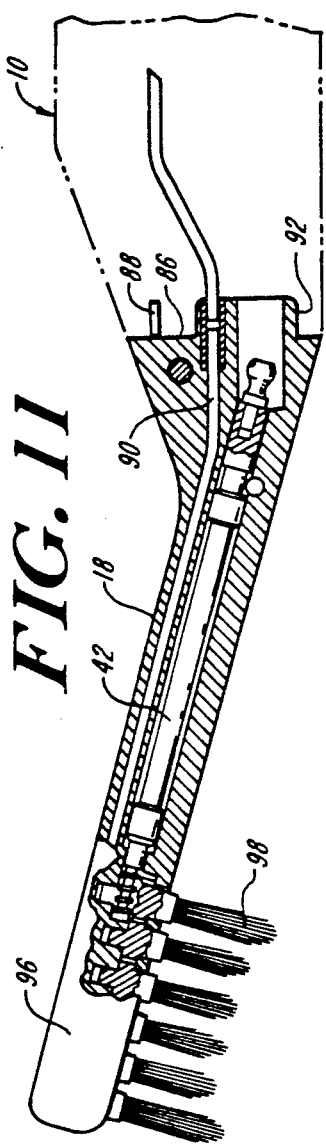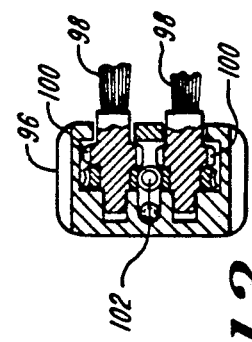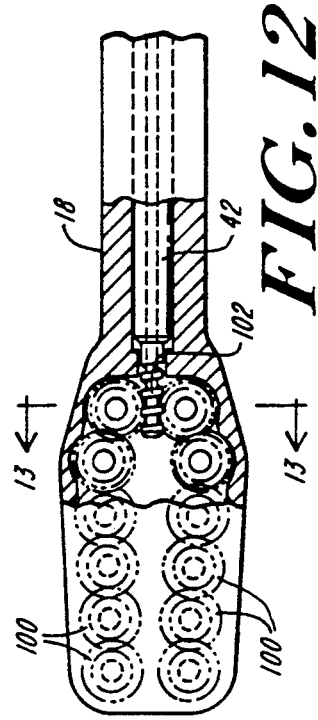

DENTAL TOOL WITH LIQUID DISPENSING, AND CARTRIDGE

This application is a continuation in part of application Ser. No. 611,898 filed 9 November, 1990, now U.S. Pat. No. 5,142,723, and owned by the assignee hereof.

BACKGROUND

This invention relates to dental hygiene devices. In particular, it provides a dental tool that can dispense dentifrice and other liquid material from a removable and replaceable cartridge.

The invention also provides a cartridge for supplying a dispensable liquid to a powered dental tool. The cartridge is initially sealed and connects readily to a dispensing tube when installed in the tool, and is readily removed for replacement.

The invention further provides a multiple treatment dental care system having a single powered handle that operates interchangeable with a fluid dispensing nozzle implement for spray and irrigation, with a rotary treatment implement, and with a revolving bristle brush implement. In addition to dispensing fluid with the nozzle implement, the system can dispense, to the dental site being treated, dentifrice or other liquid material by way of the rotary implement and by way of the revolving brush implement.

The art regarding multiple implement oral hygiene devices includes U.S. Pat. No. 4,880,382, which discloses a powered dental tool that operates with a conventional brush head, stimulators, and an interproximal floss holder.

Other art regarding dental hygiene devices includes Kieler U.S. Pat. No. 3,148,684 that discloses a toothbrush fitted with a replaceable bubble-type dispenser of toothpaste. U.S. Pat. No. 4,013,370 of Gingras discloses a toothbrush device fitted with a removable cartridge for supplying toothpaste. O'Rourke U.S. Pat. No. 4,049,354 discloses a toothbrush device fitted with a cartridge of dentifrice and which is squeezable to expel the dentifrice Cerquozzi U.S. Pat. No. 4,155,663 discloses a toothbrush device fitted with a replaceable toothpaste container, the closure of which is opened upon fitting with the brush element. Myer et al. U.S. Pat. No. 4,236,651 discloses a toothbrush device in which the handle telescopically receives a cartridge for supplying dental liquid.

Lemire U.S. Pat. No. 4,375,924 discloses a toothbrush device in which a container of toothpaste removably and replaceably attaches to the end of the brush handle. Turner U.S. Pat. No. 4,583,563 discloses a toothbrush device in which a disposable toothpaste cartridge fits within the brush handle. U.S. Pat. No. 4,695,177 of Kuo discloses a toothbrush device in which dentifrice stored in the brush handle is deposited onto the brush bristles. U.S. Pat. No. 4,717,278 of Kemeny discloses a toothbrush device in which the handle portion contains a replaceable supply of dentifrice that can be discharged onto the top of the brush bristles.

Among the objects of this invention are to provide an improved oral hygiene appliance that can dispense liquid materials to the dental implement being used or to the dental site being treated, and which further is powered to clean or otherwise treat the dental site with a powered implement.

Another object of the invention is to provide an oral hygiene appliance that is powered to drive a dental implement and that dispenses liquid material from a removable and replaceable supply cartridge. Yet another object is to provide an appliance of the above character that can selectively apply any of at least two liquids to the dental site.

Other objects of the invention include providing a cartridge for supplying liquid material to a dental tool and which can readily be removed and replaced, and which can readily be collapsed for emptying, upon installation in the dental tool.

Yet another object to the invention is to provide a dental tool that can operate with a cartridge supplying liquid material to the site being treated and alternatively can deliver a different liquid to the treatment site.

It is also an object of the invention to provide a powered dental tool that can operate with any of multiple implements including a nozzle implement, a rotary treatment implement, and a revolving bristle brush implement and, further, that can dispense liquid selectively with each treatment implement.

Further objects of the invention are to provide a dental hygiene appliance of the above character, and material-supplying cartridges of the above character, that are convenient and safe for use and that can be manufactured at relatively low cost.

Other objects of the invention will in part be obvious and will in part appear hereinafter.

SUMMARY OF THE INVENTION

A dental appliance according to the invention can dispense liquid material, such as a liquid dentifrice or medicament, to a dental site being cleaned or otherwise treated and can dispense the liquid material from a removable and replaceable cartridge. The appliance has a motorized drive mechanism for driving a dental implement that is fitted on the tool. The appliance structure thus accommodates both the motorized drive mechanism and the liquid supply mechanism, and both delivers driving power to the implement it carries and dispenses liquid by way of that implement.

According to a further feature of the invention, a removable and replaceable cartridge for supplying liquid material for dispensing in an oral hygiene appliance is selectively collapsible to facilitate expelling the liquid material. The supply cartridge, and the appliance with which it operates, are of such structure that the appliance can be used readily both with and without the cartridge, and the cartridge is readily installed and replaced.

Further, a dental appliance system according to another feature of the invention has a single handle that mounts both a powered drive mechanism and a liquid dispensing mechanism. The handle operates interchangeably with a fluid dispensing nozzle implement, with a rotary treatment implement, and with a revolving-bristle brush implement. The powered handle can dispense liquid with the nozzle implement and can dispense liquid dentifrice or other liquid material by way of the rotary implement and by way of the revolving brush implement. Yet another feature of such an embodiment of the invention is that any of at least two liquids can be dispensed, selectively.

According to one aspect of the invention, it provides dental tool apparatus having a housing with a head portion for deploying a dental tool implement, and having a first passage within the housing for the delivery of fluid material to the head portion for discharge to a dental site. The tool receives a supply of fluid material for connection with the passage and for discharge to a dental site.

The tool has a cartridge-receiving seat in the housing for receiving the supply of fluid material in a removable and replaceable cartridge element.

A cartridge-carrying transport mechanism is mounted with the housing and is movable relative to the housing between a load position and a deploy position.

The transport mechanism is arranged for the removable and replaceable loading of a cartridge element thereon and for the unloading of a cartridge element therefrom when in the load position. It is further arranged for coupling a cartridge element received thereon into fluid communication with the passage, upon movement from the load position to the deploy position, and for uncoupling a cartridge element from fluid communication with the passage, upon reverse movement to the load position.

One preferred embodiment of the tool housing has a body section elongated along an axis and has the head portion at a first axial end of the body section. Further, the tool housing carries a drive element for operating a dental tool implement. The housing is arranged with the head portion, the cartridge-receiving seat means, and the drive element axially arrayed along the axis of the housing.

According to further preferred features, the transport mechanism is hingingly movable relative to the housing, between the load and the deploy positions, about a hinge axis oriented transverse to the housing axis. The transport mechanism includes structure for selectively collapsing a cartridge element carried with the transport means for the discharge of fluid material from within the cartridge element.

In one embodiment, the transport mechanism has first and second cartridge-mounting members spaced apart thereon and arranged for mountingly engaging spaced locations on a cartridge element. It is preferred that the two cartridge-mounting members be relatively adjustably positionable on the transport mechanism for selectively adjusting the spacing between them. This adjustably positioned structure enables an operator to collapse, and alternatively to elongate, a cartridge mounted therewith.

Another aspect of the invention is that the dental tool has a further passage within the housing for the delivery of fluid material to the first passage. It also has a switch element in fluid communication with the first passage and with the further passage for selectively delivering fluid to the first passage from either the further passage or from a cartridge element carried on the transport mechanism.

It is a further feature of the invention to provide a dental tool of the foregoing character and that has a second passage within the housing for carrying fluid materials to the cartridge-receiving seat. The second passage has coupling elements arranged for selective removable and replaceable fluid communication with a fluid by-pass element carried on said transport mechanism when in the deploy position, for the transfer of fluid material between the second passage and the first passage by way of the fluid by-pass element.

The practice of the invention also provides a cartridge element for providing a removable and replaceable supply of dispensable liquid material to a dental tool, and which has a bladder element for containing liquid material to be dispensed. The bladder element is collapsible along at least a first axis for the discharge of liquid material therefrom and has first and second axial ends. There is a first fluid port at one axial end of the bladder element and which is arranged for telescopically interfitting with a fluid conduit for fluid communication therewith.

A frangible seal at the first fluid port is arranged to be opened upon the telescopic interfitting with the fluid conduit, for fluid communication between the bladder element and the conduit through the opened seal.

The cartridge element has at least a first mount at one end of the bladder means for the removable and replaceable mounting of the cartridge element. The cartridge element is arranged to receive and transmit to the bladder element a bladder-collapsing movement.

The attainment of these and other features of the invention provides a single dental appliance and system for providing multiple dental hygiene procedures for tooth care. Moreover, the dental tool provides a user operable choice of dental implement, power drive for the selected implement, and selective dispensing of liquid. These combinations of features enhance the convenience and the scope of the dental care which the invention makes possible for an individual consumer, as well as for a dentist and a professional oral hygienist.

The invention accordingly comprises the features of construction, combinations of elements and arrangements of parts exemplified in the constructions hereinafter set forth, and comprises the article of manufacture possessing the features, properties, and relation of elements exemplified in the article hereinafter described, and the scope of the invention is indicated in the claims.

For a fuller understanding of the nature and objects of the invention, reference is to be made to the following detailed description and the accompanying drawings, in which:

FIG. 1 is a pictorial view, partly disassembled, of an oral hygiene system embodying features of the invention;

FIG. 2 is a side cross-sectional view of a dental tool of the system FIG. 1;

Figure 7:
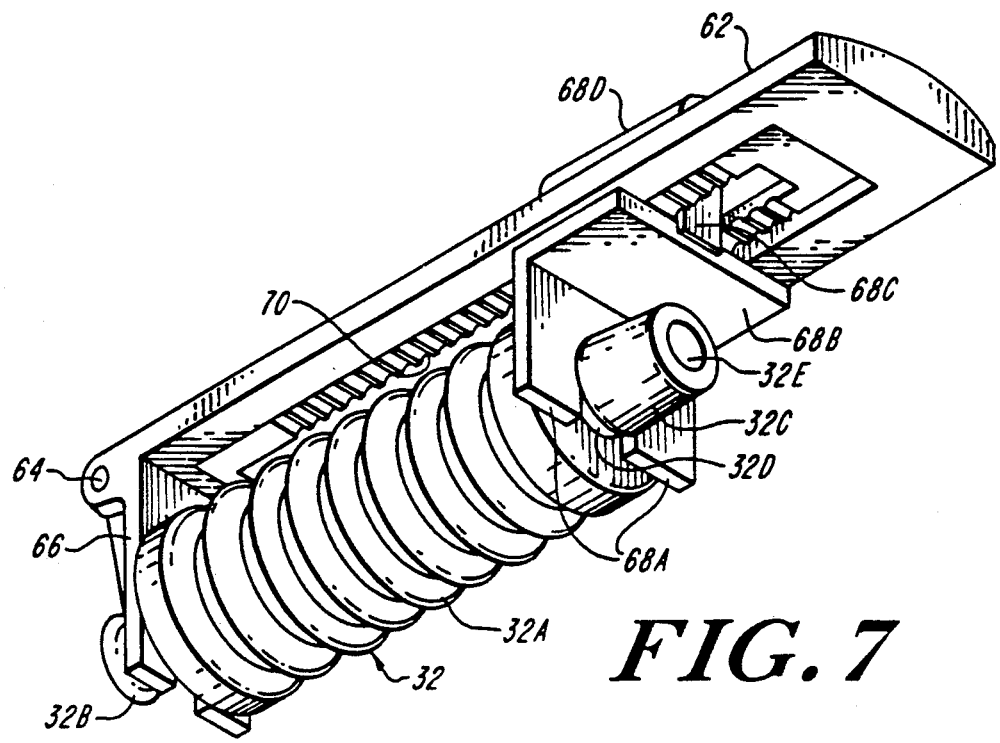
Figure 8:
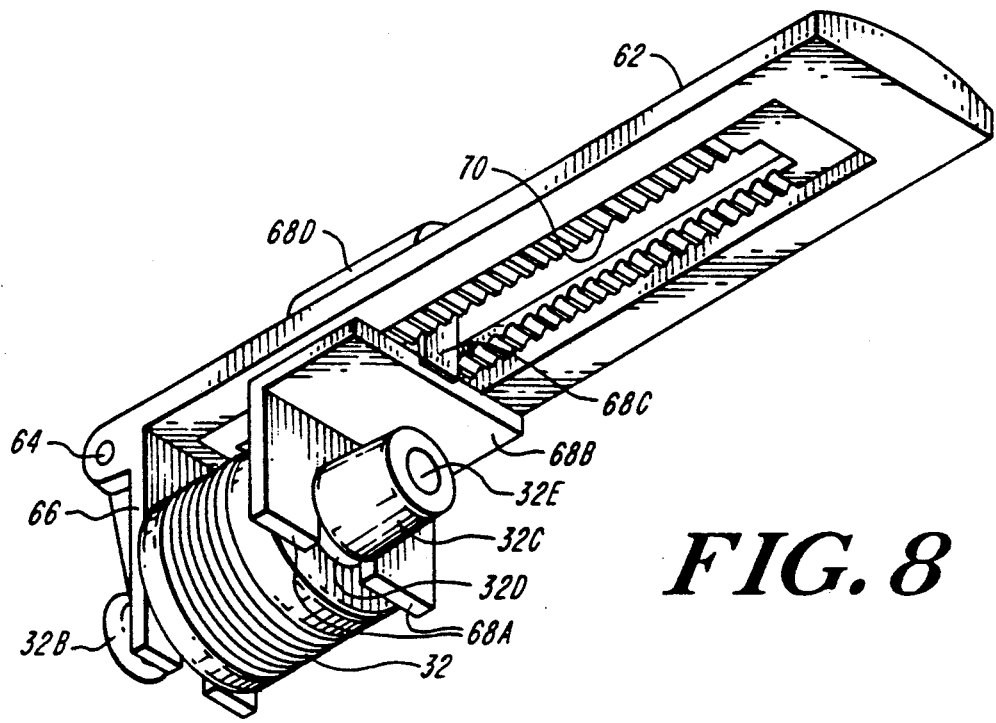
Figure 14:
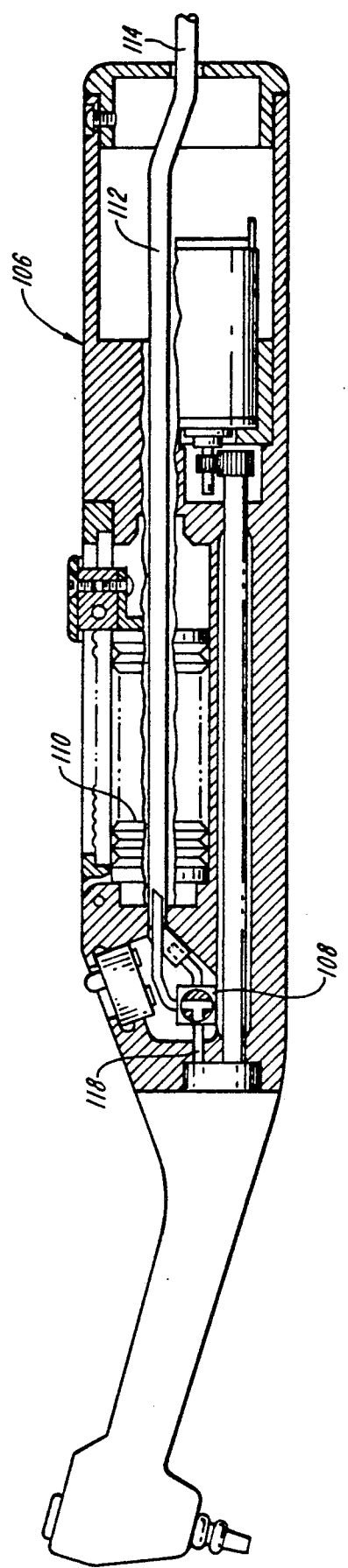

FIGS. 3, 4, and 5 are transverse cross-sectional views of the dental tool of FIG. 2 taken along section lines 3—3, 4—4, and 5—5, respectively;

FIG. 6 is a top plan view of the dental tool of FIG. 2, partly broken away;

FIGS. 7 and 8 are fragmentary perspective views showing the cartridge and cartridge transport of the dental tool of FIG. 1 in two different operating conditions;

FIG. 9 is a fragmentary cross-sectional view of the dental tool of FIG. 1, similar to FIG. 2 and showing a feed-through device installed in the cartridge bay;

FIG. 10 is a cross-sectional view of a nozzle implement for use with the system FIG. 1;

FIGS. 11, 12, and 13 are side cross-sectional and top plan and transverse sectional views, respectively, of a revolving-bristle brush implement for use with a system FIG. 1; and FIG. 14 is a view similar to FIG. 2 of another dental tool according to the invention.

DESCRIPTION OF ILLUSTRATED EMBODIMENTS

One oral hygiene system according to the invention has, as FIG. 1 shows, a hand-held power module indicated generally at 10 that can deploy any one of several dental implements, including a nozzle implement 12 for providing pulsating oral irrigation, and a rotating implement 14. The rotating implement can deploy any of several fittings, indicated generally at 16, and drive them with a rotating and reciprocating motion for providing both cleaning and stimulation. A third implement that the power module 10 can deploy is a multi-tuft rotating dental brush implement 18.

The power module 10 can discharge liquid when using the nozzle implement 12 and can discharge liquid to the dental site being treated with either implement 14 or 18. The power module 10 receives the liquid, in one instance, from a fluid container 20 seatingly fitted on a combined power source and fluid pump unit 22. The unit 22 is connected with the power module 10 by way of a combined power and fluid conduit 24. The illustrated power and pump unit 22, which operates with standard electrical line power, has an on/off control 22A and a fluid pressure control 22B. The construction of the power and pump unit 22 and its operation with the remaining elements of the system as described herein can be implemented with known skills. FIG. 1 also indicates that the power module 10 can, alternative to operation with the power and pump unit 22, operate with electrical power received by way of a portable electrical adapter 26. Further, the power module can operate with pneumatic pressure, i.e. be air driven, rather than electrically powered as illustrated.

The manual power module 10, as illustrated, houses a drive mechanism employing an electric motor 28 coupled by way of gears and a shaft 30 to rotate and reciprocate fittings attached to the rotating implement 14 and, alternatively, to rotate the bristles of the brush implement 18.

The power module 10 can, in addition, dispense liquid dentifrice or other liquid material from a disposable supply cartridge 32 that removably and replaceably seats within the power module 10.

The power module 10, shown in FIGS. 2 and 6 coupled with the rotating implement 14, has a tubular casing-like housing 34 that is elongated along an axis 36, and that mounts the implement 14 at a front axial end and internally houses the motor 28 adjacent to the other axial end. A pair of gears 38 couple the motor shaft to the drive shaft 30, which extends parallel to the axis 36. A snap-fitting universal joint 40, at the front end of the housing 34, removably and replaceably couples the drive shaft 30 to a power shaft 42 in the implement 14. Each illustrated fitting 16 can be removably and replaceably snap fitted to the lower, output end of the shaft 46 for rotation and reciprocation with the shaft 46. A pair of bevel gears 44 couples the other end of the power shaft 42 to an output shaft 46 in the implement 14. The output shaft has a cam following end 46A that engages a camming mechanism 48 to produce a selected axial reciprocation of the output shaft as it is rotated about its drive axis 50. The axis 50 of the illustrated tool is substantially transverse to the axis 36. This construction and operation of the bevel gear pair 44, shaft 46, cam follower 46A, and camming mechanism 48 in the implement 14 are described further in the commonly assigned and co-pending application for patent Ser. No. 512,836, U.S. Pat. No. 5,145,369, entitled DENTAL TOOL DRIVING APPARATUS HAVING ROTATING AND ROTO-RECIPROCATING MOTIONS, which is incorporated herein by this reference.

With further reference to FIGS. 1 and 2, motor 28, suitably operated by a manual switch accessible on the housing 34, drives the shaft 30. The resultant drive rotation is coupled, by way of the universal coupling 40 and the shaft 42, to rotate the output shaft 46 about the axis 50 and, selectively, to reciprocate the output shaft 46 longitudinally along the axis 50.

With further reference to FIGS. 2 and 6, the illustrated power module 10 has a re-entrant internal cavity 52 that removably and replaceably seats the supply cartridge 32. The cavity 52 is elongated along the housing axis 36 and openly accessible, for insertion and removal of a cartridge, at the tubular side wall of the housing 34. The illustrated cavity is located axially between the housing front end, where an implement fittingly attaches, and the forward location of the motor 28. A forward fluid conduit 54 within the housing 34 extends from a telescopic coupling 54A at the front end of the housing to a coupling 54B at the front end of the cartridge cavity 52. The forward conduit is arranged to removably and replaceably couple with a cartridge 32. A rear fluid conduit 56 extends generally axially within the housing 34 in the forward direction (right to left in FIGS. 2 and 6) from a connection with the fluid line 24A of the conduit 24 to a coupling 56A at the back end of the cartridge cavity 52. The coupling 56A is arranged for selective fluid coupling with a cartridge 32 seated in the cavity 52.

The housing 34 mounts a lever mechanism indicated generally at 60 for loading and alternatively unloading a cartridge 32. The illustrated lever mechanism includes a lever arm 62 mounted with a hinge 64 to the housing 34 adjacent to the axially forward end of the cavity 52 for rotation about an axis transverse to the housing axis 36 and, in the illustrated embodiment, to the implement axis 50. With further reference to FIGS. 2, 6, and 7, the lever arm 62 extends rearward from, and axially of, the hinge 64 to a closed or deploy position, shown in solid lines in FIGS. 2 and 6, where it closes the cavity 52 and deploys the cartridge for dispensing the liquid contents. A bifurcated cartridge-mounting frontal bracket 66 extends transversely from the lever arm 62 adjacent the frontal hinge end, and a second bifurcated mounting bracket 68 extends from the arm 62 parallel to the bracket 66. The bracket 68 is movably mounted on the lever arm 62, for movement along the length of the arm 62. The illustrated movable mounting bracket 68 has, in addition to a pair of mounting fingers 68a, a platform portion 68b that fits along the underside of the arm 62, as shown in FIG. 7. A web 68c extends on the bracket 68 from the platform portion 68b outwardly through an axially extending slot 70 in the lever arm 62 to an enlarged manual actuator 68d disposed on the outer side of the lever arm 62. The opposed surfaces of the bracket platform 68b and the arm 62 carry interfitting ratchet-like teeth. A leaf compression spring 72 is carried on the manual actuator 68d and compressively bears between the actuator and the outer surface of the lever arm 62, to urge the two interfitting ratcheted surfaces of the bracket platform and the lever arm into engagement.

FIGS. 1 and 7 show that the illustrated cartridge 32 has a concertina-like tubular bellows chamber 32a that is axially collapsible and expandable and is fitted at each axial end with a coupling 32b, 32c. Each coupling includes a stem 32d of reduced diameter that removably and replaceably snap fits between the mounting fingers of a mounting bracket 66, 68. The neck is axially between an enlarged flange-like surface formed by the bellows chamber 32a and a further enlarged flange surface on the coupling. The engagements of these flange surfaces with each mounting bracket 66 and 68 enable axial movement of the mounting bracket 68 to axially collapse a bellows, to the collapsed condition shown in FIG. 8, and conversely to extend it axially, to the Position shown for example in FIG. 9.

Each cartridge coupling 32b and 32c further has a central bore 32e for removably and replaceably telescopically fitting with one corresponding fluid conduit 54 and 56 in the housing 34.

With this structure of the cartridge 32 and of the lever mechanism 60, the lever arm 62 is moved to an open or load position, shown in broken lines in FIGS. 1 and 2, for loading a cartridge into the module 10. The movable mounting bracket 68 is moved rearward on the lever arm 62 and a cartridge is installed to the lever arm by snap fitting the cartridge couplings 32b and 32c to the lever mounting bracket 66 and 68 respectively, as appears in FIG. 7. The lever arm 62 is then hingedly moved to the closed position, shown in solid lines in FIGS. 1 and 2. This movement carries the mounted cartridge 32 into the cavity 52. It also moves the front coupling 32b of the cartridge axially forward and telescopically seats the coupling 32b over and axially onto the coupling 54b of the forward fluid conduit 54. This conduit coupling can include a sharpened end for piercing and thereby opening a frangible seal within the cartridge.

Thus, closing the lever mechanism, by moving the lever arm 62 from the opened position to the closed position, both installs a cartridge into the housing cavity, and places the interior of the cartridge in fluid communication with the forward conduit 54. The liquid contents of the cartridge 32 can then flow into the forward fluid conduit 54 for dispensing through whatever implement is fitted to the power module 10.

The cartridge can be progressively collapsed by the user, by manually pressing the actuator 68d radially inward, i.e inwardly on the modular housing 34, and simultaneously moving the actuator axially forward on the housing, thereby moving the removable mounting bracket 68 forward. This action collapses the bellows chamber 32a and thereby compresses the liquid contents to be expelled from the cartridge into the forward fluid conduit 54. FIG. 8 illustrates the condition of a cartridge 32 when fully collapsed by this manual manipulation of the lever mechanism 60.

A supply cartridge 32, whether spent or otherwise to be removed, can be removed from the module 10 by opening the mechanism 60, i.e. raising the lever arm 62 from the closed position to the open position, and then removing the cartridge from its mounting with the brackets 66 and 68.

The illustrated power module 10 can feed liquid to the forward fluid conduit 54 directly from the rear fluid conduit 56, in lieu of feeding liquid from a supply cartridge 32, by replacing a liquid-containing supply cartridge 32 with a feed-through cartridge 74, shown in FIG. 1. This feed-through cartridge 74 has couplings 74b and 74c that correspond to the supply cartridge couplings 32b and 32c, respectively. In lieu of a bellows-like chamber, the illustrated feed-through cartridge 74 simply has an axially flexible conduit 74a for communicating liquid between the ports at the couplings 74b and 74c.

The feed-through cartridge 74 can be loaded, by way of the lever mechanism 60, in the same manner as described above for a supply cartridge 32. However, after the lever mechanism is closed, a further step for use of the feed-through cartridge is to depress the lever mechanism actuator 68d and move it axially backward, thereby elongating the feed-through cartridge 74 to place the rear coupling 74c into telescopic fluid communicating engagement with the coupling 56a of the rear fluid conduit; see FIG. 9. When a feed-through cartridge 74 is thus installed, it provides fluid communication between the rear conduit 56 and the forward conduit 54. The power module 10 then couples liquid received on the fluid line 24a of the conduit 24 to the implement, typically the nozzle implement 12, for discharge to a dental site by way of that implement.

The removal of the feed through cartridge 74 involves an initial step of releasing the communication between the coupling 74c and the rear fluid conduit 56, by depressing and moving forward the actuator 68d on the lever mechanism. The lever arm 62 can then be opened and the feed-through cartridge replaceably removed in the same manner as a supply cartridge 32.

Alternative to using the feed-through cartridge 74 to couple liquid from the conduit 56 to the conduit 54, a supply cartridge 32 can be used. That is, a supply cartridge 32, preferably empty of the liquid it normally supplies, can be installed in the module 10, and elongated to connect the coupling 56a to the cartridge coupling 32c.

With reference to FIGS. 1, 2, and 6, the illustrated power module 10 has, for the removable and replaceable mounting of an implement 12, 14, or 18, a flat coupling surface 80 at the forward axial end. The surface 80 is recessed with a receptacle seat 82, within which the forward end of the drive shaft 30 and one fitting of the universal coupling 40 extend and are accessible, as appears in FIG. 1. Further, an alignment aperture 84 recesses the coupling surface 80, and the forward coupling 54a of the fluid conduit 54 is disposed within the receptacle seat 82.

Correspondingly, each illustrated implement 12, 14, and 18 has, at its axially back end, a flat coupling surface 86 for seating against the housing coupling surface 80. A mounting plug 92 projects axially from the coupling surface 86 for telescopically seating within the housing receptacle seat 82. An alignment pin 88 projects from the implement for alignment seating within the housing aperture 84. Further, each implement that has a fluid conduit 90 therein has a coupling 90a on the conduit that telescopically fits on, with fluid communication, the housing coupling 54a.

Further, where the implement has a power shaft, such as the power shaft 42 of the rotating implement 14 shown in FIG. 2, the section of the coupling 40 on that shaft is disposed for engaging the mating element of the coupling 40 which is carried on the module drive shaft 30.

Thus, each illustrated implement is fitted onto the power module 10 by first aligning the implement with the module and seating the alignment pin 88 within the alignment aperture 84. Upon further telescopic interfitting, the fluid conduits and the drive and power shafts interconnect. Conversely, an implement is removed from the module 10 by axially moving them apart to first release the mechanical and fluid engagements and then to release the alignment engagement. It will be apparant that other know structures, including a bayonet-type coupling, can be used on the module 10 and on each implement 12, 14 or 18, to mount the implement for operation on the module 10.

The nozzle implement 12, illustrated in FIG. 10, has a nozzle-forming hollow stem 96 that receives liquid from the housing by way of the housing conduit 54 and the implement conduit 90, when coupled with the power module. The nozzle implement has the module mounting structure described above with an alignment pin 88, mounting plug 92, and coupling 90a on the fluid conduit 90. The implement 12 can dispense liquid with an irrigating stream, a spray or other discharge.

The illustrated rotating brush implement 18 has, as FIGS. 11, 12, and 13 show, the above-described structure for mounting to the power module 10 including a coupling surface 86 from which a mounting plug 92 axially projects, and from which the alignment Pin 88 also projects. A fluid conduit 90 and a power shaft 42 are disposed as described above for operative coupling with corresponding elements of the power module 10.

At the forward end of the stem 96 of this brush implement 18, multiple bristle tufts 98 are mounted, each for rotation. Each bristle tuft has a gear at its end that is seated within the stem 96, and the several gears are successively engaged, as appears in FIG. 12, to form two sequences of engaged bristle gears 100, 100. A worm gear 102 at the forward end of the power shaft 42 engages these two trains of matched gears so that rotation of the power shaft 42 rotatingly drives the bristle tufts.

Among the many variations with which the invention can be practiced are, as shown in FIG. 14, a module 106 having a selector mechanism, illustrated as employing a two-way directional valve 108 arranged for coupling, to whatever implement is mounted on the module 106, either liquid from an installed supply cartridge 110 or liquid from the fluid line 112 of the conduit 114. In the selection mechanism of FIG. 14, the fluid line 112 feeds to one input of the two-input directional valve 108. The other valve input is connected to receive liquid from the cartridge 110, and the valve feeds either input liquid to the forward fluid coupling 118. The one-way valve 108 operates in response to the pressures of the liquids it receives from the cartridge 110 and from the fluid line 112. One alternative to the illustrated directional valve 108 is a valve operated manually by the user to select which liquid to apply to the forward coupling 118. In a further embodiment, the selector mechanism employs a valve that is automatically placed in the proper position, i.e. for feeding either liquid from the cartridge 110 or liquid from the fluid line 112 to the forward fluid coupling 118 according to the implement coupled with the power module 106. That is, the implement-module interface in this alternative embodiment can include a mechanism on the module 106 that responds to the particular implement to which the module is fitted for placing the fluid selector in the corresponding position.

It will thus be seen that the invention efficiently attains the objects set forth above, among those made apparent from the preceding description and the drawings. Since certain changes may be made in the above constructions without departing from the scope of the invention, it is intended that all matter containing the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and secured by Letters Patent is:

1. In dental tool apparatus having a housing with a head portion for deploying a dental tool implement, and
having a first passage within said housing for the delivery of fluid material to said head portion for discharge to a dental site,
the improvement comprising
A. means forming a cartridge-receiving seat in said housing for receiving a supply of fluid material in a removable and replaceable cartridge element, and
B. cartridge-carrying transport means movably mounted with said housing and movable relative to said housing between a load position and a deploy position, said transport means being mounted with said housing in both said load position and said deploy position,
C. said transport means being arranged for the removable and replaceable loading of a cartridge element thereon and the unloading of a cartridge element therefrom when in said load position, and being further arranged for coupling a cartridge element received thereon into fluid communication with said passage upon movement from said load position to said deploy position and for uncoupling a cartridge element from fluid communication with said passage upon movement to said load position.

2. In dental tool apparatus according to claim 1, the further improvement wherein
said housing has a body section elongated along an axis and has said head portion at a first axial end of said body section.

3. In dental tool apparatus according to claim 2, the further improvement wherein
A. said housing carries drive means for operating a dental tool implement, and
B. said housing is arranged with said head portion, said cartridge-receiving seat means, and said drive means being axially arrayed along said axis of said housing.

4. In dental tool apparatus according to claim 3, the further improvement wherein
said housing is arranged with said cartridge-receiving seat means disposed between said head portion and said drive means.

5. In dental tool apparatus according to claim 2, the further improvement in which
said transport means is hingingly movable relative to said housing, between said load and deploy positions.

6. In dental tool apparatus according to claim 1, the further improvement in which
said transport means includes means for selectively collapsing a cartridge element, said means for collapsing being carried with said transport means for the discharge of fluid material from within the cartridge element.

7. In dental tool apparatus according to claim 1, the further improvement wherein
said transport means has first and second cartridge-mounting means spaced apart thereon and arranged for mountingly engaging spaced locations on a cartridge element.

8. In dental tool apparatus according to claim 7, the further improvement in which
said first and second cartridge-mounting means are relatively adjustably positionable on said transport means for selectively adjusting the spacing therebetween.

9. In dental tool apparatus according to claim 1, the further improvement comprising
   A. means forming a further passage within said housing for the delivery of fluid material to said first passage, and
   B. switch means in fluid communication with said first passage and with said further passage for selectively delivering to said first passage fluid from either said further passage or fluid from a cartridge element carried on said transport means.

10. In dental tool apparatus according to claim 1, the further improvement comprising
   means forming a second passage within said housing for carrying fluid materials to said cartridge-receiving seat means, said second passage having coupling means arranged for selective removable and replaceable fluid communication with fluid-guiding means carried on said transport means when in said deploy position, for the transfer of fluid material between said second passage and said first passage by way of the fluid-guiding means.

11. In dental tool apparatus
having a housing with a head portion for deploying a dental tool implement, and
having a first passage within said housing for the delivery of liquid material to said head portion for discharge to a dental site,
the improvement comprising
   A. means forming a cartridge-receiving seat in said housing for receiving a supply of liquid material in a removable and replaceable cartridge element,
   B. cartridge-carrying transport means rotationally movably mounted with said housing and movable relative to said housing between a load position and a deploy position,
   C. said transport means being arranged for the removable and replaceable loading of a cartridge element thereon and the unloading of a cartridge element therefrom when in said load position, and being further arranged for coupling a cartridge element received thereon into liquid communication with said first passage upon movement from said load position to said deploy position and for uncoupling a cartridge element from liquid communication with said first passage upon movement to said load position, and
   D. liquid-supplying cartridge means removably and replaceably mounted with said transport means for movement therewith between said load position and said deploy position and, when in said deploy position, in liquid communication with said first passage.

12. In dental tool apparatus
having a housing with a head portion for deploying a dental tool implement, and
having a first passage within said housing for the delivery of liquid material to said head portion for discharge to a dental site,
the improvement comprising
   A. said housing having a body section elongated along a body axis and said head portion being disposed at a first axial end of said body section,
   B. means forming a cartridge-receiving seat in said housing body section for receiving a supply of liquid material in a removable and replaceable cartridge element,
   C. cartridge-carrying transport means mounted with said housing and movable relative to said housing between a load position and a deploy position, said transport mans being arranged for the removable and replaceable loading of a cartridge element thereon and the unloading of a cartridge element therefrom when in said load position, and being further arranged for coupling a cartridge element received thereon into liquid communication with said first passage upon movement form said load position to said deploy position and for uncoupling a cartridge element from liquid communication with said first passage upon movement to said load position,
   D. liquid-supplying cartridge means removably and replaceably mounted with said transport means for movement therewith between said load position and said deploy position and, when in said deploy position, in liquid communication with said first passage, said cartridge means being collapsible, along a selected further axis, for dispensing liquid therefrom, and
   E. said transport means having first and second cartridge-engaging elements movably spaced apart along said further axis and arranged for selectively changing the spacing therebetween for accommodating full cartridge means and for selectively collapsing cartridge means carried with said transport means for the dispensing of liquid from the cartridge means.

13. In dental tool apparatus
having a housing with a head portion for deploying a dental tool implement, and
having a first passage within said housing for the delivery of liquid material to said head portion for discharge to a dental site,
the improvement comprising
   A. means forming a cartridge-receiving seat in said housing for receiving a supply of liquid material in a removable and replaceable cartridge element,
   B. cartridge-carrying transport means mounted with said housing and movable relative to said housing between a load position and a deploy position,
   C. said transport means being arranged for the removable and replaceable loading of a cartridge element thereon and the unloading of a cartridge element therefrom when in said load position, and being further arranged for coupling a cartridge element received thereon into liquid communication with said first passage upon movement from said load position to said deploy position and for uncoupling a cartridge element from liquid communication with said first passage upon movement to said load position,
   D. liquid-supplying cartridge means removably and replaceably mounted with said transport means for movement therewith between said load position and said deploy position and, when in said deploy position, in liquid communication with said first passage
   E. means forming a second passage in said housing for the delivery of fluid material to said cartridge-receiving seat means, and
   F. said transport means being arranged for selectively coupling said cartridge means into fluid communication with said second passage, when in said deploy position, for placing said first and second fluid passages in fluid communication by way of said cartridge means.

14. In dental tool apparatus according to claim 13, the further improvement
   A. in which said housing has a body section elongated along a body axis,
   B. in which said transport means is hingingly movable relative to said housing along a hinge axis oriented transversely to said body axis and has a first end proximal to a body first end and has a second end distal from said body first end and movable with said hinged movement,
   C. in which said transport means has cartridge mounting means arranged for removably and replaceably mountingly said cartridge means, and
   D. wherein said cartridge mounting means are adjustably movable for the selective collapse of said cartridge means.

15. In dental tool apparatus
having a housing with a head portion for deploying a dental tool implement, and
having a first passage within said housing for the delivery of fluid material to said head portion for discharge to a dental site,
the improvement comprising
   A. means forming a cartridge-receiving seat in said housing for receiving a supply of fluid material in a removable and replaceable cartridge element, arranged for removable and replaceable connection with said first passage, and
   B. means forming a further passage in said housing arranged for the delivery of fluid material to a cartridge element received in said cartridge receiving seat,
   C. whereby fluid material can be delivered to a cartridge element from said further passage and can be delivered to said first passage from a cartridge element.

16. In dental tool apparatus
having a housing with a head portion for deploying a dental tool implement, and
having a first passage within said housing for the delivery of fluid material to said head portion for discharge to a dental site,
the improvement comprising
dispensing means carried with said housing for receiving a supply of fluid material in a removable and replaceable cartridge element and being movable relative to said housing between a load position and a deploy position, said dispensing means being arranged for the removable and replaceable loading of a cartridge element thereon and for the unloading of a cartridge element therefrom when in said load position, and being further arranged for removably and replaceably coupling a cartridge element received thereon into fluid communication with said first passage upon movement from said load position to said deploy position and for uncoupling a cartridge element from fluid communication with said first passage, said dispensing means being mounted with said housing throughout said movement between said load and said deploy positions.

17. In apparatus according to claim 16, the further improvement comprising manually-operable means for controlling the discharge of fluid from a cartridge element that is coupled in fluid communication with said first passage.

* * * * *